United States Patent [19]

Allen et al.

[11] Patent Number: 4,999,493

[45] Date of Patent: Mar. 12, 1991

[54] ELECTROSPRAY IONIZATION INTERFACE AND METHOD FOR MASS SPECTROMETRY

[75] Inventors: Mark Allen, Houston, Tex.; Ivor A. S. Lewis, London, England

[73] Assignee: Vestec Corporation, Houston, Tex.

[21] Appl. No.: 514,658

[22] Filed: Apr. 24, 1990

[51] Int. Cl.$^5$ .................. H01J 49/04; H01J 49/10
[52] U.S. Cl. ......................... 250/288; 250/282
[58] Field of Search ................. 250/281, 282, 288

[56] References Cited

U.S. PATENT DOCUMENTS

| 4,023,398 | 5/1977 | French et al. | 73/23 |
| 4,209,696 | 6/1980 | Fite | 250/281 |
| 4,531,056 | 6/1985 | Labowsky et al. | 250/288 |
| 4,842,701 | 6/1989 | Smith et al. | 204/180.1 |
| 4,885,076 | 12/1984 | Smith et al. | 204/299 R |

FOREIGN PATENT DOCUMENTS 84302752 10/1984 European Pat. Off. .
1246709 9/1971 United Kingdom .

OTHER PUBLICATIONS

Article–"Negative Ion Production with the Electrospray Ion Source", Yamashita et al., J. Phys. Chem. 1984, 88, 4671–4675.
Article–"Ion Pumping and Free Jet Expansion", Whitehouse et al., pp. 857–864.
Article–"Capillary Zone Electrophoresis-Mass . . . Ionization Interface", Smith et al., Anal., Chem., 1988, 60, 436–441.
Articl;e–"Improved Electrospray Ionization . . . Mass Spectrometry", Smith et al., 60 Anal. Chem. 1988, 1948–1952.
Article–"An Electrospray Ionization Mass Spectrometer with New Features", Chowdhury et al., Rapid Communications In Mass Spec. 82.
Article–"Electrospray on Magnetic Instruments", Allen et al., Rapid Communications in Mass Spectrometry, vol. 3, No. 8, 1989.

Primary Examiner—Jack I. Berman
Attorney, Agent, or Firm—Browning, Bushman, Anderson & Brookhart

[57] ABSTRACT

Improved techniques are provided for forming ionized molecules from electrosprayed droplets for analysis by a mass spectrometer. A high voltage is applied to a capillary tube for spraying droplets at substantially atmospheric pressure or above, and the electrosprayed droplets contain sample solute of interest and solvent. The electrosprayed droplets are passed into an ion generating chamber which is maintained at a pressure in the range of from 0.2 Torr to 10 Torr. The walls of the ion generating chamber are controllably heated to a temperature which will desolvate the droplets and produce ionized molecules of interest for analysis by the mass spectrometer. The electrospray technique does not rely upon a countercurrent heated gas flow, and provides a particularly simple and inexpensive means to couple electrospray ionization to either quadrupole or magnetic mass analyzers.

17 Claims, 1 Drawing Sheet

...

ELECTROSPRAY IONIZATION INTERFACE AND METHOD FOR MASS SPECTROMETRY

BACKGROUND OF THE INVENTION

1. Field of the Invention

The present invention relates to techniques for producing ions for analysis of chemical compositions. More particularly, the present invention relates to improved techniques for ionizing electrospray droplets containing molecules of interest and solvent for mass spectrometric analysis of various chemical compounds.

2. Description of the Background

Mass spectrometry (MS) has long been a widely accepted analytical technique in the chemical sciences field to obtain qualitative and quantitative information from a sample. MS is commonly used to determine molecular weight, identify chemical structures, and accurately determine the composition of mixtures. MS is becoming increasingly important in biological research to determine the structure of organic molecules based on the fragmentation pattern of ions formed when sample molecules are ionized. According to MS, individual molecules may be "weighed" by ionizing the molecules and measuring the response of their trajectory to electric or magnetic fields. Improved techniques have been developed to analyze thermally unstable or nonvolatile molecules with high molecular weights over 10,000 Daltons.

Large molecules cannot be readily transformed into gas phase ions suitable for MS analysis using electron ionization, photo-ionization, and chemical ionization techniques due to the extensive decomposition of the molecules which occurs in these processes. Such extensive decomposition substantially reduces the accuracy of the analytical technique, and accordingly these ionization techniques are not generally preferred for analysis of large molecules. Intact ions from large molecules are increasingly being produced by "soft" ionization techniques, however, including field desorption, electrohydrodynamic ionization, thermospray, and electrospray. These soft ionization techniques do not significantly alter the molecules of interest, and are becoming increasingly used in conjunction with gas phase analyzers to determine the composition of samples. While each of these soft ionization techniques is preferred by certain users, electrospray is one of the more promising soft ionization techniques for the efficient production of ions for mass spectrometric analysis.

Electrospray ionization techniques were first proposed in the late 1960's. A sample solution containing molecules of interest and a solvent is pumped through a hypodermic needle and into an electrospray chamber. An electrical potential of several kilovolts may be applied to the needle for generating a fine spray of charged droplets. According to UK patent specification No. 1,246,709, the droplets may be sprayed at atmospheric pressure into a chamber containing a heated gas to vaporize the solvent. Alternatively, the needle may extend into an evacuated chamber, and the sprayed droplets then heated in the evacuated chamber by an infared filament. In either case, ions are focused into a beam, which is accelerated by an electric field gradient, and the ions then analyzed in a mass spectrometer.

Significant disadvantages are encountered if an electrospray is discharged into an evacuated chamber. The charged droplets are not retarded from migrating toward the chamber walls, thereby increasing the possibility of discharge and disruptions to the spray. U.S. Pat. No. 4,209,696 teaches an electrospray technique which occurs at atmospheric pressure or above, and the produced ions are input to a mass analyzer.

Although the electrospray jet is formed at atmospheric pressure, mass spectrometers or other gas phase detectors routinely operate within a vacuum chamber. A vacuum housing for the mass spectrometer typically includes a plurality of lenses in a vacuum chamber maintained at a low pressure of several Torr or less. The chamber is typically heated to about 100° C. to keep the chamber and lenses clean. The gaseous components of the jet which are emitted into the mass spectrometer first pass through these lenses having orifices sized to maintain the desired pressure in view of the practical limitations of the vacuum pumps. A small percentage of the ions produced in the electrospray chamber pass through these orifices and into the analyzer, since most of the ions are removed with the solvent vapor by the vacuum pumps. Accordingly, the transfer efficiency (percentage of ions produced by the electrospray which actually enter the analyzer) is low, which substantially limits the sensitivity of the electrospray/MS technique.

Another significant problem with electrospray concerns the condensation of the expanding jet and clustering of the ions. To reduce this problem, heated counterflow gases are commonly employed to vaporize sprayed droplets and desolvate ions at atmospheric pressure. Since the heated counterflow gases remove much of the solvent vapor from the stream of gas before being drawn into the vacuum chamber, this technique increases the concentration of ions of interest in the vacuum chamber. U.S. Pat. No. 4,023,398 teaches a technique whereby ions pass through an orifice into a vacuum chamber, while a gas curtain upstream from the orifice reduces transmission of solvent vapor into the vacuum chamber. The gas is heated to hasten evaporation of the solvent from the droplets, thereby producing desolvated ions at substantially atmospheric pressure. U.S. Pat. No. 4,531,056 teaches a similar technique, whereby an inert gas is introduced into the electrospray chamber in a direction opposite to a flow from the capillary. The electrospray chamber remains at or slightly greater than atmospheric pressure. Ions of interest are produced within the electrospray chamber, and the inert gas flow substantially reduces the concentration of solvent vapor which enters the analyzer. U.S. Pat. Nos. 4,842,701 and 4,885,076 disclose a system which combines capillary zone electrophoresis with electrospray for gas analysis of an analyte mixture. Again, the electrospray occurs at atmospheric pressure, and a heated countercurrent gas flow technique is used to desolvate the spray droplets.

While the counterflowing gas concept described above results in reasonable sensitivity, it substantially increases the complexity of the interface between the electrospray and the mass spectrometer. In order that the solvent vapor from the evaporating droplets be efficiently removed by the counterflowing gas, both the temperature and the flow rate of the gas must be carefully controlled. High gas flow rates may prevent some ions with low mobility from entering the analyzer, while low gas flow rates or reduced gas temperature may not sufficiently desolvate the ions. The counterflowing gas flow rate and temperature are typically optimized for each analyte and solvent. Accordingly, much trial and error time is necessary to determine the optimum gas flow rate and temperature for each particular analyte utilizing a particular electrospray device and a particular gas analyzer.

The disadvantages of the prior art are overcome by the present invention, and improved techniques are hereinafter disclosed utilizing electrospray techniques for improved ionization of molecules of interest to enhance the reliability and sensitivity of the mass spectrometric or other gas-phase analysis.

SUMMARY OF THE INVENTION

Improved methods and apparatus are provided for analyzing liquid effluent which includes a sample solute of interest and a solvent (or mixture of solvents). The solute may consist of high molecular weight organic molecules, which are input preferentially with a volatile solvent, such as methanol. The techniques of the present invention may be used with various gas phase detectors, and are particularly well suited for quadrupole or magnetic field mass spectrometers.

According to the present invention, the solute is discharged from a syringe needle into an electrospray chamber maintained at approximately atmospheric pressure. A high electrical potential is applied to the needle with respect to the housing walls to produce a spray containing highly charged droplets. At atmospheric pressure and at normal room temperature, these charged droplets rapidly vaporize and disintegrate to produce molecular ions in equilibrium with the vapor present in the chamber. So long as sufficient air or other dry gas is available within the electrospray chamber to keep the partial pressure of vapor low, then essentially all of the sprayed liquid droplets are substantially if not completely vaporized within the electrospray chamber. The quantity of gas added to the electrospray chamber should be sufficient to maintain the desired atmospheric pressure within the electrospray chamber and prevent discharge of the droplets to the electrospray housing walls.

The sprayed droplets, the solvent vapor, and any added gas are discharged from the electrospray chamber through a restricted aperture, and into an ion generating chamber. The walls of the ion generating chamber are heated to maintain a temperature within the chamber of at least 120° C., and preferably between 150° C. and 250° C. The ion generating chamber is connected to a vacuum pump to maintain a low pressure in the range of from 0.2 Torr to 10 Torr.

Adiabatic expansion of the fluid, which consists of partially or totally desolvated ions and vapor, through the restricted aperture and into the ion generating chamber rapidly cools the fluid and causes the solvent vapor to condense on the ions, thereby producing large clusters. To counteract this effect, the present invention discloses heating the ion generating chamber to desolvate the ions cluster of and produce molecular ions suitable for analysis by a mass spectrometer. These ions are then efficiently transferred to a mass spectrometer for determining qualitative or quantitative information about the solute molecules.

It is an object of the present invention to provide an inexpensive and versatile technique for producing and transmitting molecular ions to a mass spectrometer for analysis.

Another object of the invention is to form charged spray droplets by electrospray techniques, to vaporize the charged droplets, and to produce molecular ions and desolvate cluster of ions by the application of heat to the walls of an ion generating chamber downstream from a electrospray chamber, with the ion generating chamber being maintained at a pressure of about 10 Torr or less.

It is a feature of this invention that its concepts are applicable to both quadrupole and magnetic deflection mass spectrometers.

It is another feature of the present invention that a gas may be added to the electrospray chamber to maintain the electrospray capillary tube at a desired temperature, and to maintain at least substantially atmospheric pressure within the electrospray chamber.

It is another feature of the invention that all of the fluid which exits the electrospray chamber, including solvent vapor, ions, and added gas, exit through a restricted aperture into a partially evacuated ion generating chamber.

It is a further feature of the present invention that the ion generating chamber is heated in a controlled manner so as to efficiently desolvate the molecular ions without causing fragmentation or pyrolysis.

These and further objects, features, and advantages of the present invention will become apparent from the following detailed description, wherein reference is made to the figures in the accompanying drawings.

DETAILED DESCRIPTION OF PREFERRED EMBODIMENTS

Figure 1:
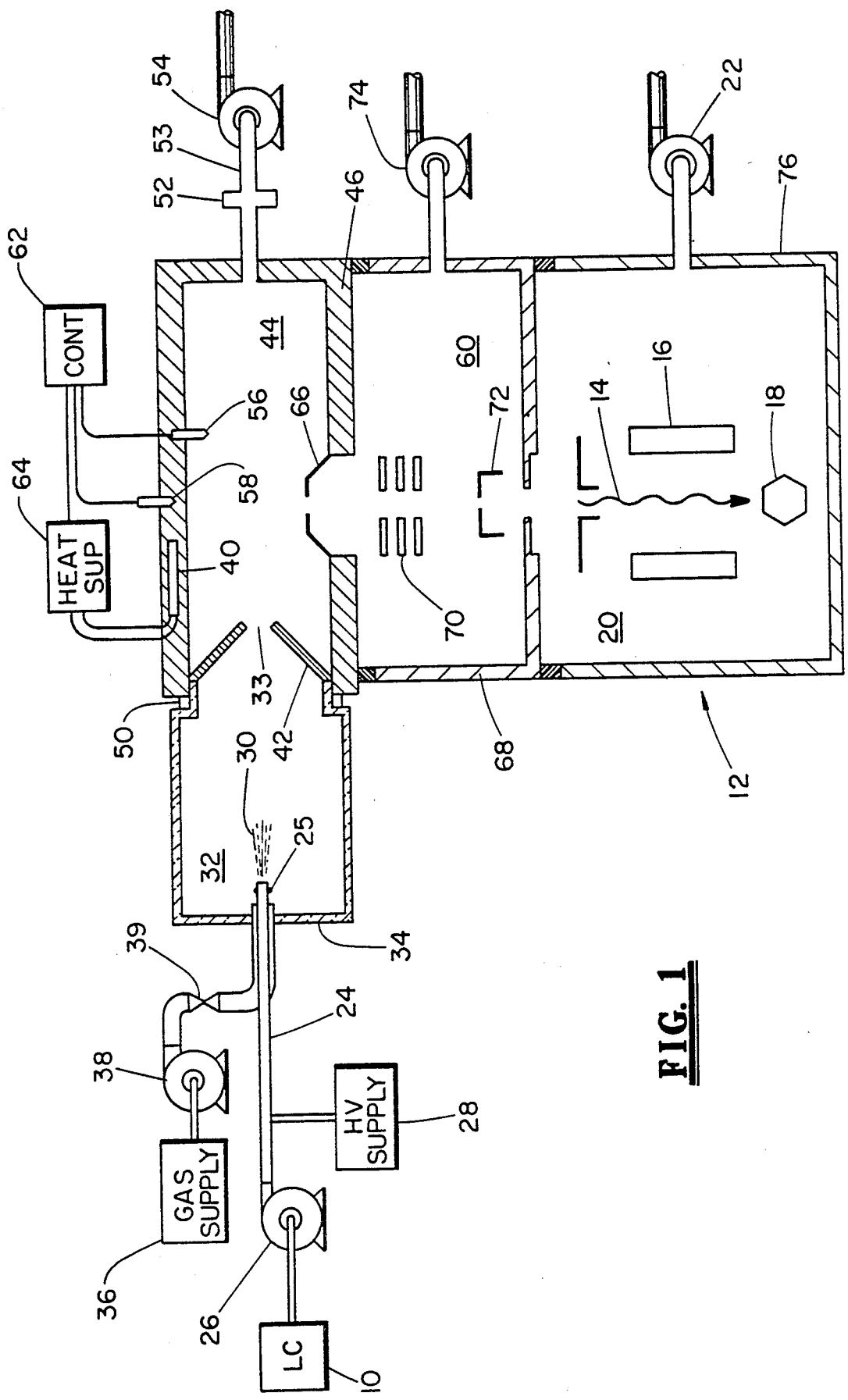
FIG. 1 is a simplified pictorial view and block diagram of one embodiment of an electrospray and ionization interface according to the present invention between a liquid chromatograph and a mass spectrometer.

FIG. 1 depicts a suitable apparatus or interface for converting effluent from a liquid chromatograph 10 to ionize molecules of interest suitable for analysis by a mass spectrometer 12. The mass spectrometer 12 may be of various types, although either a quadrupole mass analyzer, such as depicted in FIG. 1, or a magnetic deflection analyzer (not shown) is preferred. In either case, the analyzer 12 may receive a beam 14 of ions which are selectively transmitted according to their mass-to-charge ratio to an electron multiplier detector 18. For the ions to be transmitted between four conventional quadrupole rods 16 to the detector, and for the mass analyzer and electron multiplier detector to operate properly, the mass analyzer is housed within a chamber 20 which is maintained at a vacuum of less than about $10^{31 5}$ Torr by vacuum pump 22 with a pumping speed of approximately 150 liters per second.

The effluent from the liquid chromatograph 10 is passed through a stainless steel syringe needle or capillary tube 24. According to the present invention, a uniform spray may be formed when pump 26 delivers a liquid effluent through the tube 24, e.g., at flow rates of a few microliters per minute. A high voltage power source 28 is electrically coupled to the conductive capillary tube 24 to maintain the tube at a potential of from 1 KV to 10 KV, and preferably between 2 KV and 5 KV relative to the nozzle portion 42 which defines the discharge port 33 from the electrospray housing. The nozzle portion 42, in turn, may be maintained at the same potential as the ion generating housing 46, which is typically at a potential of only 5 to 20 volts relative to ground for a quadrupole analyzer, or at a high potential of, for example, 8 KV relative to ground in the case of a magnetic analyzer. The solution is electrosprayed as a jet 30 of charged droplets into electrospray chamber 32 formed by electrospray housing 34. The effluent consist of molecules of interest (solute) and solvent vapor. The capillary tube 24 and thus the jet 30 are axially movable within the electrospray chamber 32, to selectively control the distance between the spray 30 and the port 33.

A gas, such as air or nitrogen, from supply 36 may optionally be input axially into the electrospray chamber 32 by pump 38. The volume of input gas may be controlled by valve 39 to maintain the desired pressure within the chamber 32 at substantially atmospheric pressure. The gas may be introduced at various places into the electrospray chamber, but if introduced axially over the needle 24 it should be diverted from the needle tip by deflector 25 so that it does not aerodynamically interfere with formation of the electrospray. All fluids entering the chamber 32 escape through the discharge port 33, which is aligned with the axis of that portion of tube 24 within the chamber 32. The size of the aperture 33 is controlled to maintain substantially atmospheric pressure within the chamber 32, since a reduction in pressure, e.g., to less than 100 Torr, would enhance discharge of the sprayed droplets onto the walls of the housing 34.

The electrospray housing 34 may be formed from an electrically insulating material, such as glass, to aid in directing the electrospray jet toward the discharge port 33, and to allow direct visual observation of the spray. Forming the electrospray housing from an electrically insulating material is particularly convenient when the invention is used with a magnetic deflection mass analyzer in which the ion generating chamber may be maintained at up to 8 KV from ground. Alternatively, the walls of the electrospray housing 34 may be electrically conductive and isolated from the nozzle portion 42 which defines the discharge port 33, and a variable potential applied to the housing to assist in directing the electrospray jet toward the discharge port. An insulating material 50 may be used to electrically isolate the ion generating housing 46 from the electrospray housing 34.

All the fluid which enters the electrospray chamber 32 is discharged through the restricted port 33 into the ion generating chamber 44. Although most of the electrospray droplets are desolvated within the electrospray chamber, adiabatic expansion of this fluid into the ion generating chamber 44 rapidly cools the fluid, causing the solvent vapor to condense on the ions and produce clusters of ions which are not suitable for analysis. To counteract this effect, at least a portion of the ion generating housing 46 is heated by electrical heating elements 40. Power to the elements 40 is supplied from supply source 64, which in turn is regulated by controller 62. The controller 62 is preferentially responsive to thermocouple 56 placed within the ion generating chamber, and optionally may be controlled by thermocouple 58 which monitors the temperature of the electrospray housing 46. The temperature of the ion generating chamber 44 may thus be closely controlled in a manner as disclosed in U.S. Pat. No. 4,814,612 for direct heating of the walls of a thermospray expansion chamber. The ion generating chamber is heated to a temperature of at least 120° C. and preferably between 150° C. and 250° C., to desolvate the ions and avoid clustering.

The ion generating chamber 44 is connected to vacuum pump 54 for maintaining a low pressure in the range of from 0.2 Torr to 10 Torr within the chamber 44. A restrictive insert 52 may be provided in the pumpout line 53 from the ion generating chamber, which preferentially is maintained in the range of from 0.5 Torr to 3 Torr.

The desolvated ions pass from the ion generating chamber 44 through the sampling cone 66 and enter the ion optics chamber 60 formed by housing 68. The interface unit may have an orthogonal geometry as shown in FIG. 1, or gas flow of the sprayed droplets and desolvated ions from the electrospray needle 24 to the mass spectrometer 12 may remain coaxial. A plurality of beam focusing plates 70 and located disks 72 are provided within the ion optics chamber 60 for directing the ions to the analyzer 12. The vacuum pump 74 maintains a pressure of less than $10^{31\ 3}$ Torr within the chamber 60. Since the desolvation of the electrosprayed droplets occurs in chamber 44 at a substantially reduced pressure, a substantial spacing may be provided between the discharge port 33 of the electrospray chamber 32 and the passageway through the sampling cone 66 where the ions enter the ion optics chamber 60.

A mass spectrometer housing 76 is typically maintained at ground potential and, as previously noted, the ion generating chamber 44 and the discharge port 33 are typically maintained at only 5-20 volts relative to ground when used with a quadrupole mass spectrometer, and may be from 3 to 8 KV in the case of a magnetic mass spectrometer. An additional 2 5 KV is applied to the electrospray needle 24 relative to the discharge port 40. The present invention, particularly in the embodiment using an insulating material such as glass for the body of the electrospray housing 34, allows the necessary potentials to be maintained without causing undersirable gaseous discharges to occur.

The foregoing disclosure and description of the invention is illustrative and explanatory of the techniques of the present invention and various changes in the size and shape, of the interface, as well as the details of the illustrated construction, may be made within the scope of the appended claims without departing from the spirit of the invention.

What is claimed is:

1. Apparatus for converting a liquid effluent including sample solute of interest and solvent into ionized molecules for analysis of the sample by a mass spectrometer, the apparatus comprising:
   (a) an electrospray unit for receiving liquid effluent and for discharging charged droplets, the electrospray unit including
      (i) an electrospray housing defining an atmospheric pressure electrospray chamber therein,
      (ii) a capillary tube for passing liquid effluent therethrough, the capillary tube having an exit within the electrospray chamber for discharging sprayed droplets containing sample solute of interest and solvent,
      (iii) a voltage source for applying a voltage to the capillary tube to produce charged sprayed droplets containing sample solute of interest and solvent, the charged sprayed droplets vaporizing within the electrospray housing to produce ions, and
      (iv) a restricted discharge port through the electrospray housing for outputting the ions and solvent vapor from the electrospray chamber, the discharge port being sized to maintain substantially atmospheric pressure within the electrospray chamber during spraying; and (b) an ion generating unit for receiving clusters of ions including condensed solvent from the electrospray unit and for discharging ionized molecules to the mass spectrometer, the ion generating unit including
  (i) an ion generating housing defining an ion generating chamber therein,
  (ii) an ion generating unit vacuum pump for maintaining pressure within the ion generating chamber in the range of from 0.2 Torr to 10 Torr,
  (iii) a temperature sensor for monitoring the temperature within the ion generating chamber, and
  (iv) a heating unit responsive to the temperature sensor for heating the ion generating housing to a temperature of at least 120° C. to vaporize condensed solvent in the clusters of ions and produce desolvated ionized molecules of interest for analysis by the mass spectrometer.

2. The apparatus as defined in claim 1, wherein:
the ion generating unit vacuum pump maintains a pressure in the ion generating chamber in the range of from 0.5 Torr to 3 Torr.

3. The apparatus as defined in claim 1, further comprising:
an ion optics housing defining an ion optics chamber therein and having an input port for receiving ionized molecules of interest and an output port for outputting ionized molecules of interest to the mass spectrometer:
an ion optics chamber vacuum pump for maintaining a pressure of less than 0.001 Torr within the ion optics chamber, and
lenses within the ion optics chamber for directing ionized molecules of interest toward the output port.

4. The apparatus as defined claim 1, wherein the discharge port from the electrospray housing is adjoining the ion generating chamber, such that substantially all ions and solvent vapor passing through the discharge port enter the ion generating chamber.

5. The apparatus as defined in claim 1, further comprising:
gas supply means for inputting a gas into the electrospray chamber; and
valve means for controlling the input gas to maintain substantially atmospheric pressure within the electrospray chamber.

6. The apparatus as defined in claim 5, wherein:
the capillary tube within the electrospray chamber has an axis passing substantially through the discharge port; and
the gas supply means inputs the sweep gas into the electrospray chamber in a direction substantially coaxial with the capillary tube within the electrospray chamber.

7. The apparatus as defined in claim 1, wherein the voltage source applies a voltage of from 1 KV to 10 KV to the capillary tube with respect to the ion generating housing.

8. An apparatus as defined in claim 1, wherein the mass spectrometer is a quadrupole mass analyzer.

9. The apparatus as defined in claim 1, wherein the mass spectrometer is a magnetic mass analyzer.

10. The apparatus as defined in claim 1, wherein the capillary tube is selectively movable with respect to the electrospray housing.

11. A method of converting a liquid effluent including sample solute of interest and solvent into ionized molecules for analysis by a mass spectrometer, the method comprising:
forming an electrospray chamber having a restricted discharge port therethrough:
passing liquid effluent through a capillary tube terminating within the electrospray chamber for discharging sprayed droplets containing sample solute of interest and solvent;
applying a voltage to the capillary tube to produce charged sprayed droplets containing sample solute of interest and solvent;
maintaining the electrospray chamber at substantially atmospheric pressure or above during spraying;
forming in an ion generating housing which defines an ion generating chamber;
passing the charged sprayed droplets into the ion generating chamber while maintaining a pressure within the ion generating chamber within the range of from 0.2 Torr to 10 Torr;
monitoring the temperature within the ion generating chamber; and
heating the ion generating housing in response to the monitored temperature to vaporize solvent in clusters of ions and produce desolvated ionized molecules of interest for analysis by the mass spectrometer.

12. The method as defined in claim 11, further comprising:
heating the ion generating housing to maintain a temperature within the ion generating chamber of at least 120° C.

13. The method as defined in claim 11, further comprising:
forming the electrospray chamber such that the discharge port adjoins the ion generating chamber, and substantially all fluid exiting the electrospray chamber enter the ion generating chamber.

14. The method as defined in claim 11, further comprising:
inputting a gas to the electrospray chamber; and
controlling the quantity of input gas to maintain substantially atmospheric pressure within the electrospray chamber.

15. The method as defined in claim 14, further comprising:
inputting the gas into the electrospray chamber in a direction substantially coaxial with the capillary tube within the electrospray chamber.

16. The method as defined in claim 11, further comprising:
applying the voltage of from 1 KV to 10 KV to the capillary tube with respect to the ion generating housing.

17. The method as defined in claim 11, further comprising:
selectively moving the terminal end of the capillary tube within the electrospray housing.

* * * * *